US008469966B2

(12) United States Patent
Allen et al.

(10) Patent No.: US 8,469,966 B2
(45) Date of Patent: Jun. 25, 2013

(54) SYSTEMS, METHODS, AND APPARATUSES FOR TENSIONING AN ORTHOPEDIC SURGICAL CABLE

(75) Inventors: C. Wayne Allen, Southaven, MS (US); Jaime E. Martinez, Pompton Plains, NJ (US)

(73) Assignee: Smith & Nephew, Inc., Memphis, TN (US)

( * ) Notice: Subject to any disclaimer, the term of this patent is extended or adjusted under 35 U.S.C. 154(b) by 1075 days.

(21) Appl. No.: 11/233,892

(22) Filed: Sep. 23, 2005

(65) Prior Publication Data

US 2006/0167464 A1    Jul. 27, 2006

Related U.S. Application Data

(60) Provisional application No. 60/612,380, filed on Sep. 23, 2004.

(51) Int. Cl.
*A61B 17/58* (2006.01)
*A61B 17/60* (2006.01)
*A61F 2/00* (2006.01)

(52) U.S. Cl.
USPC ........................................................ 606/103

(58) Field of Classification Search
USPC .. 606/103, 263, 74; 623/13.13; 254/237–238, 254/243, 245–247; 279/2.02–2.04, 4.07–4.09
See application file for complete search history.

(56) References Cited

U.S. PATENT DOCUMENTS 575,631 A    1/1897    Brooks
902,040 A    10/1908   Wyckoff (Continued)

FOREIGN PATENT DOCUMENTS

DE    43 43 117 A1    6/1995
DE    196 29 011 A1   1/1998

(Continued)

OTHER PUBLICATIONS

Baumgaertel, et al., "Fracture healing in biological plate osteosynthesis," *Injury*, 29(Supp. 3):S-C3-S-C6 (1998).

(Continued)

*Primary Examiner* — Jan Christopher Merene
*Assistant Examiner* — Michelle C Eckman
(74) *Attorney, Agent, or Firm* — Kilpatrick Townsend & Stockton LLP

(57) ABSTRACT

Systems, methods, and apparatuses for tensioning an orthopedic surgical cable used in conjunction with an orthopedic implant device, a bone, and/or bone implant or structure. At least one device in accordance with various embodiments of the invention includes a handheld body handheld body capable of receiving a portion of the orthopedic surgical cable. The handheld body includes a clamping body adapted to restrain a first portion of the orthopedic surgical cable with an adjustable gripping force, wherein a tension is placed on the orthopedic surgical cable. The handheld body also includes an adjusting mechanism adapted to cooperate with the clamping body to change the gripping force on the orthopedic surgical cable. In addition, the handheld body includes a slide adapted to change the position of the clamping body relative to the handheld body. Furthermore, the handheld body includes a force application member operably connected to the slide, wherein the slide is adapted to be manipulated in order to change the position of the clamping body in a manner whereby the tension is subject to gradual control by manipulation of the slide and force application member, and whereby the handheld body and orthopedic surgical cable are adapted to allow the orthopedic surgical cable to be tensioned by the clamping body at a first tension, and further adapted to allow the orthopedic surgical cable to be subsequently tensioned by the slide and force application member at a second tension without loss of tension.

23 Claims, 5 Drawing Sheets

U.S. PATENT DOCUMENTS

| | | | |
|---|---|---|---|
| 1,641,077 A * | 8/1927 | Fouquet | 140/121 |
| 2,501,978 A | 3/1950 | Wichman | |
| 3,507,270 A * | 4/1970 | Ferrier | 600/481 |
| 3,866,607 A | 2/1975 | Forsythe et al. | |
| 3,975,032 A * | 8/1976 | Bent et al. | 279/30 |
| 4,441,563 A * | 4/1984 | Walton, II | 173/213 |
| RE31,628 E | 7/1984 | Allgower et al. | |
| 4,484,570 A | 11/1984 | Sutter et al. | |
| 4,712,773 A * | 12/1987 | Larson | 256/25 |
| 5,027,867 A * | 7/1991 | O'Connor | 140/123.5 |
| 5,057,113 A * | 10/1991 | Mingozzi | 606/103 |
| 5,085,660 A | 2/1992 | Lin | |
| 5,199,146 A * | 4/1993 | Grover et al. | 29/268 |
| 5,230,129 A * | 7/1993 | Scruggs | 29/267 |
| 5,275,601 A | 1/1994 | Gogolewski et al. | |
| 5,312,410 A * | 5/1994 | Miller et al. | 606/86 R |
| 5,324,291 A | 6/1994 | Ries et al. | |
| 5,387,217 A * | 2/1995 | Sefcik et al. | 606/103 |
| 5,395,374 A * | 3/1995 | Miller et al. | 606/74 |
| 5,415,658 A * | 5/1995 | Kilpela et al. | 606/300 |
| 5,423,820 A | 6/1995 | Miller et al. | |
| 5,431,659 A * | 7/1995 | Ross et al. | 606/103 |
| 5,454,821 A * | 10/1995 | Harm et al. | 606/148 |
| 5,470,333 A | 11/1995 | Ray | |
| 5,527,310 A | 6/1996 | Cole et al. | |
| 5,536,127 A | 7/1996 | Pennig | |
| 5,540,698 A * | 7/1996 | Preissman | 606/103 |
| 5,569,253 A | 10/1996 | Farris et al. | |
| 5,601,553 A | 2/1997 | Trebing et al. | |
| 5,609,596 A | 3/1997 | Pepper | |
| 5,665,088 A | 9/1997 | Gil et al. | |
| 5,676,667 A | 10/1997 | Hausman | |
| 5,702,399 A | 12/1997 | Kipela et al. | |
| 5,709,686 A | 1/1998 | Talos et al. | |
| 5,772,663 A * | 6/1998 | Whiteside et al. | 606/74 |
| 5,788,697 A | 8/1998 | Kilpela et al. | |
| 5,893,856 A | 4/1999 | Jacob et al. | |
| 5,902,305 A * | 5/1999 | Beger et al. | 606/103 |
| 5,935,130 A | 8/1999 | Kipela et al. | |
| 5,935,133 A | 8/1999 | Wagner et al. | |
| 5,954,722 A | 9/1999 | Bono | |
| 5,964,769 A | 10/1999 | Wagner et al. | |
| 5,968,046 A | 10/1999 | Castleman | |
| 6,053,921 A | 4/2000 | Wagner et al. | |
| 6,129,730 A | 10/2000 | Bono et al. | |
| 6,176,861 B1 | 1/2001 | Bernstein et al. | |
| 6,193,721 B1 | 2/2001 | Michelson | |
| 6,206,881 B1 | 3/2001 | Frigg et al. | |
| 6,235,033 B1 | 5/2001 | Brace et al. | |
| 6,251,111 B1 * | 6/2001 | Barker et al. | 606/86 A |
| 6,306,136 B1 | 10/2001 | Baccelli | |
| 6,306,140 B1 | 10/2001 | Siddiqui | |
| 6,322,562 B1 | 11/2001 | Wolter | |
| 6,355,043 B1 | 3/2002 | Adam | |
| 6,358,250 B1 | 3/2002 | Orbay | |
| 6,361,537 B1 | 3/2002 | Anderson | |
| 6,364,885 B1 | 4/2002 | Kilpela et al. | |
| 6,391,030 B1 | 5/2002 | Wagner et al. | |
| 6,413,259 B1 | 7/2002 | Lyons et al. | |
| 6,428,542 B1 | 8/2002 | Michelson | |
| 6,440,135 B2 | 8/2002 | Orbay et al. | |
| 6,454,769 B2 | 9/2002 | Wagner et al. | |
| 6,475,218 B2 | 11/2002 | Gournay et al. | |
| 6,506,191 B1 | 1/2003 | Joos | |
| 6,520,965 B2 | 2/2003 | Chervitz et al. | |
| 6,595,994 B2 | 7/2003 | Kilpela et al. | |
| 6,623,486 B1 | 9/2003 | Weaver et al. | |
| 6,682,533 B1 | 1/2004 | Dinsdale et al. | |
| 6,730,091 B1 | 5/2004 | Pfefferle et al. | |
| 6,821,278 B2 | 11/2004 | Frigg et al. | |
| 6,960,213 B2 | 11/2005 | Chervitz et al. | |
| 6,974,461 B1 | 12/2005 | Wolter | |
| 7,160,310 B2 * | 1/2007 | Nesper et al. | 606/148 |
| 7,326,222 B2 * | 2/2008 | Dreyfuss et al. | 606/144 |
| 7,704,252 B2 * | 4/2010 | Albertson et al. | 606/74 |
| 8,096,998 B2 * | 1/2012 | Cresina | 606/103 |
| 2001/0037112 A1 | 11/2001 | Brace et al. | |
| 2001/0047174 A1 | 11/2001 | Donno et al. | |
| 2002/0032450 A1 * | 3/2002 | Trudeau et al. | 606/103 |
| 2002/0045901 A1 | 4/2002 | Wagner et al. | |
| 2002/0058940 A1 | 5/2002 | Frigg et al. | |
| 2002/0058943 A1 * | 5/2002 | Kilpela et al. | 606/74 |
| 2002/0072753 A1 * | 6/2002 | Cohen | 606/103 |
| 2002/0091391 A1 * | 7/2002 | Cole et al. | 606/72 |
| 2002/0143338 A1 | 10/2002 | Orbay et al. | |
| 2003/0018335 A1 | 1/2003 | Michelson | |
| 2004/0044345 A1 | 3/2004 | DeMoss et al. | |
| 2004/0073218 A1 | 4/2004 | Dahners | |
| 2004/0087954 A1 | 5/2004 | Allen et al. | |
| 2004/0138666 A1 | 7/2004 | Molz, IV et al. | |
| 2004/0199169 A1 | 10/2004 | Koons et al. | |
| 2005/0070904 A1 | 3/2005 | Gerlach | |
| 2005/0107796 A1 | 5/2005 | Gerlach et al. | |
| 2006/0149265 A1 | 7/2006 | James | |
| 2006/0276804 A1 * | 12/2006 | Molz et al. | 606/103 |
| 2007/0162020 A1 | 7/2007 | Gerlach | |
| 2008/0208223 A1 | 8/2008 | Kraemer | |
| 2008/0234679 A1 | 9/2008 | Sarin et al. | |
| 2008/0300599 A1 | 12/2008 | Anapliotis et al. | |
| 2009/0082821 A1 * | 3/2009 | Konno et al. | 606/86 A |

FOREIGN PATENT DOCUMENTS

| | | |
|---|---|---|
| EP | 0 355 035 B1 | 2/1990 |
| EP | 0 486 762 B1 | 5/1995 |
| EP | 0 468 192 B1 | 9/1996 |
| EP | 0 760 632 B1 | 3/1997 |
| EP | 1169971 | 1/2002 |
| FR | 2 757 370 | 6/1998 |
| WO | WO 01/19264 A2 | 3/2001 |
| WO | WO 01/19267 A1 | 3/2001 |
| WO | WO 01/91660 | 12/2001 |
| WO | WO 02/058574 | 8/2002 |
| WO | WO 02/096309 A1 | 12/2002 |
| WO | WO 2005/032386 A1 | 4/2005 |
| WO | WO 2006/007965 A1 | 1/2006 |

OTHER PUBLICATIONS

Bolhofner, et al., "The Results of Open Reduction and Internal Fixation of Distal Femur Fractures Using a Biologic (Indirect) Reduction Technique," *Journal of Orthopaedic Trauma*, 10(6):371-377 (1996).

Farouk, et al., "Minimally invasive plate osteosynthesis and vascularity: preliminary results of a cadaver injection study," *Injury*, 28(Supp. 1):S-A7-S-A12 (1997).

Farouk, et al., "Minimally Invasive Plate Osteosynthesis: Does Percutaneous Plating Disrupt Femoral Blood Supply Less Than the Traditional Technique?", *Journal of Orthopaedic Trauma*, 13(6):401-406 (1999).

Frigg, et al., "The development of the distal femur Less Invasive Stabilization System (LISS)," *Injury, Int. J. Care Injured*, 32(S-C24-31 (2001).

Frigg, et al. "LCP: The Locking Compression Plate System," *Bone Zone* (undated).

Gerber, et al., "Biological internal fixation of fractures," *Arch. Orthop. Trauma Surg.*, 109:295-303 (1990).

Karnezis, et al., "'Biological' internal fixation of long bone fractures: a biomechanical study of a 'noncontact' plate system," *Injury*, 29(9):689-695 (1998).

Koval, et al., "Distal Femoral Fixation : A Biomechanical Comparison of the Standard Condylar Buttress Plate, a Locked Buttress Plate, and the 95-Degree Blade Plate," Journal of Orthopaedic Trauma, 11(7):521-524 (1997).

Krettek, et al., "Minimally invasive percutaneous plate osteosynthesis (MIPPO) using the DCS in proximal and distal femoral fractures," *Injury*, 28(Supp. 1):S-A20-S-A30 (1997).

Krettek, et al., "Intraoperative control of axes, rotation and length in femoral and tibial fractures," *Injury*, 29(Supp. 3):S-C-29-S-C39 (1998).

Marti, et al., "Biomechanical Evaluation of the Less Invasive Stabilization System for the Internal Fixation of Distal Femur Fractures," *Journal of Orthopaedic Trauma*, 15(7):482-487, 2001.

Miclau, et al., "A Mechanical comparison of the Dynamic Compression Plate, Limited Contact-Dynamic Compression Plate, and Point Contact Fixator," *Journal of Orthopaedic Trauma*, 9(1):17-22 (1995).

Mudgal, et al., 'Plate and Screw Design in Fractures of the Hand and Wrist,' *Clinical Orthopaedics and Related Research*, 445:68-80 (2006).

Rüedi, et al., "New Techniques in Indirect Reduction of Long Bone Fractures," *Clinical Orthopaedics and Related Research*, No. 347:27-34 (1998).

Schavan, et al., "LISS—The Less Invasive Stabilization System for Metaphyseal Fractures of Femur and Tibia," *OTA 98 Posters* (1998).

Brochure entitled Introducing Peak™ Polyaxial Anterior Cervical Plate, by Depuy Motech, one page, undated.

Brochure entitled Introducing the Profile™ Anterior Thoracolumbar Compression Plate, by Dupuy Motech, one page, undated.

Brochure entitled Quantum Medical Concepts, Tension Booster™ 'A simple device that will help reduce wrist fatigue. It's the little things that can make a difference,' 10 pages, powered by blanco media (undated) http://www.quantummedicalconcepts.com/home.cfm.

* cited by examiner

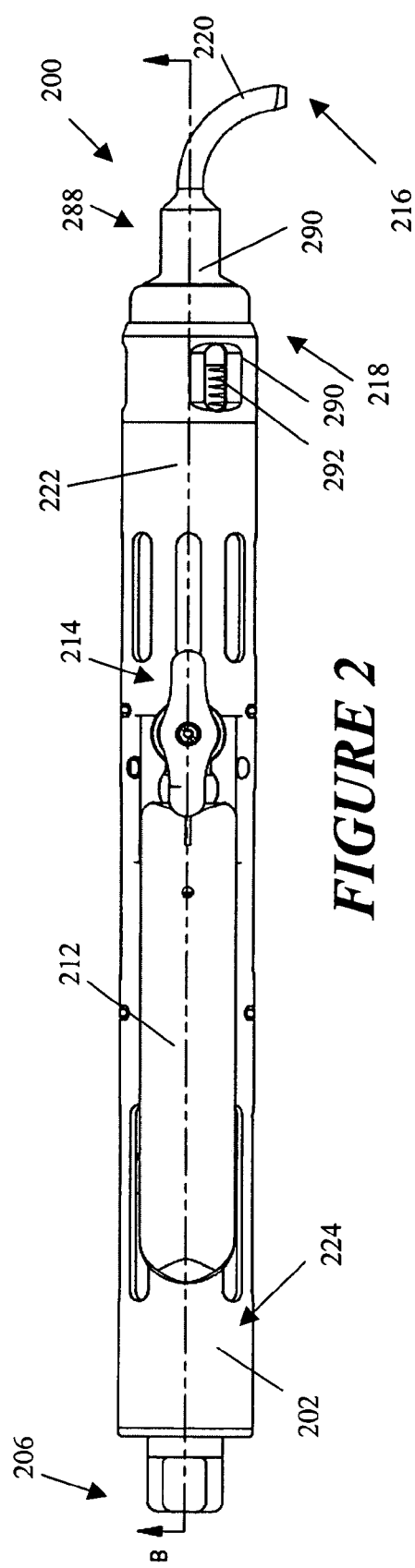
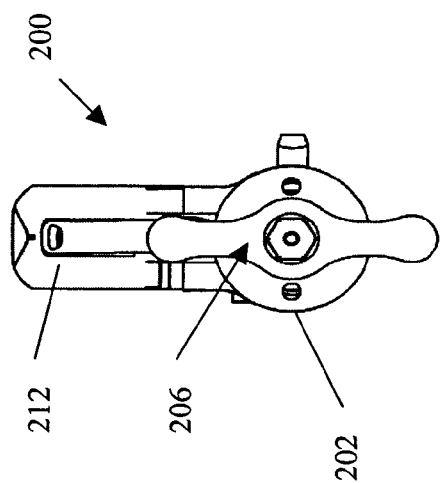
FIGURE 2
FIGURE 3

SYSTEMS, METHODS, AND APPARATUSES FOR TENSIONING AN ORTHOPEDIC SURGICAL CABLE

RELATED APPLICATIONS

This application claims priority to U.S. Provisional Ser. No. 60/612,380, entitled "Cable Tensioner," filed on Sep. 23, 2004, which is incorporated by reference.

FIELD OF THE INVENTION

The invention relates generally to systems, methods, and apparatuses related to cable tensioning devices, and more specifically to systems, methods, and apparatuses for tensioning an orthopedic surgical cable used in conjunction with an orthopedic implant device, a bone, and/or bone implant or structure.

BACKGROUND OF THE INVENTION

In an orthopedic surgical procedure, surgically implanted orthopedic cables are frequently used to secure bones together, or otherwise used to tie or fit other parts of the body together. An orthopedic surgical cable is typically a thin length of cable that is manufactured from a biocompatible material such as cobalt chromium alloy, or stainless steel, or another similar type of material. Generally, an orthopedic surgical cable is wrapped around an affected area of a patient's bone structure and then secured with a device such as a cable crimping device or cable clamping device in order to stabilize the bone, secure fractures, stabilize trauma, install other devices to the bone, and for other purposes. Conventional orthopedic surgical cable products and procedures can utilize a tensioning device such as a cable tensioning device to increase the tension on an orthopedic surgical cable in order to secure the orthopedic surgical cable with a sufficient or defined tension around the affected area of a patient's body. However, tensioning the cable can cause damage to the patient's body if the cable is overly tensioned. In other instances, the tension on the orthopedic surgical cable may be insufficient and the cable must be retightened or retensioned to obtain a sufficient tension. In any instance, a user may be limited in the use of his or her hands during the surgical procedure, and using a cable tensioning device may require both hands to utilize the cable tensioning device to apply and increase the tension on an orthopedic surgical cable. Therefore, tensioning the orthopedic surgical cable using conventional cable tensioning devices and procedures can be time consuming for the surgeon and increases costs due to excessive procedural time.

For example, one conventional orthopedic cable tensioning device utilizes an inline pen-type device with a cam. An initial tension can be placed on an orthopedic surgical cable by applying the cam to the cable. To secure the orthopedic surgical cable with the cam, the cam must be rotated from an unclamped position to a clamped position. When the cam is rotated to a clamped position adjacent to an orthopedic surgical cable, the cam provides a predefined amount of force on the orthopedic surgical cable. Once the cam is in a clamped position with respect to the orthopedic surgical cable, no additional force can be applied to the orthopedic surgical cable by the cam. In some instances, the predefined amount of force may not be sufficient to restrain the orthopedic surgical cable, and the cable may slip with respect to the cam. In this instance, a user may not be able to place tension on the cable.

In some instances, a conventional orthopedic cable product and an orthopedic surgical cable are used in conjunction with an orthopedic device, a patient's bone, bone implant, or other structure. For example, an orthopedic device such as a trochanteric grip, can be secured to the exterior surface of a patient's femur using one or more orthopedic cables and corresponding conventional orthopedic cable products or devices. Each time an orthopedic surgical cable is tensioned with respect to the patient's femur, the trochanteric grip becomes further secured to the exterior of the patient's femur. However, as each orthopedic surgical cable is tensioned, other previously tensioned orthopedic surgical cables may loosen, or the position of the orthopedic device may shift. In either instance, previously tensioned orthopedic cables may have to be re-tensioned or re-positioned with respect to the trochanteric grip and the patient's femur. Conventional orthopedic surgical cable products or devices used to secure the position of the orthopedic surgical cables may have to be replaced along with the orthopedic surgical cables that have become damaged or crushed due to the installation of the orthopedic surgical cable products or devices.

SUMMARY OF THE INVENTION

Systems, methods, and apparatuses according to various embodiments of the invention address some or all of the above issues and combinations thereof. They do so by providing a surgical cable tensioning device for tensioning and retensioning an orthopedic surgical cable used in conjunction with an orthopedic implant device, a bone, and/or bone implant or structure. The surgical cable tensioning device does not damage the orthopedic surgical cable when then the surgical cable tensioning device is operated or the surgical cable is tensioned or retensioned. While the surgical cable tensioning device is operated or in use, a tension can be placed and maintained on the orthopedic surgical cable without loss of tension. Furthermore, the surgical cable tensioning device can be reused along with the same surgical cable when the surgical cable tensioning device is unclamped and reclamped with respect to the surgical cable, while retensioning the surgical cable with respect to an orthopedic implant device, a bone, and/or bone implant or structure. Such systems, methods, and apparatuses are particularly useful for surgeons installing an orthopedic surgical cable within a patient's body, and attempting to tension and retension the orthopedic cable with respect to the installation of an orthopedic implant device, a bone, and/or bone implant or structure in the patient's body.

One aspect of systems, methods, and apparatuses according to various embodiments of the invention, focuses on apparatuses for tensioning an orthopedic cable for installation in a patient's body. For purposes of this document, such apparatuses are each known as a "surgical cable tensioning device." A surgical cable clamp tensioning device permits a surgeon to save time and reduce wastage during a surgical procedure by providing the option to operate a surgical cable tensioning device clamp with one or both hands, and reuse an orthopedic surgical cable that may have been initially installed and tensioned. The surgeon may find that later during the same surgical procedure, the orthopedic surgical cable should be retensioned, and the surgical cable tensioning device permits the surgeon to retension the orthopedic cable with respect to the installation of an orthopedic implant device, a bone, and/or bone implant or structure in a patient's body.

According to another aspect of the invention, systems, methods, and apparatuses according to various embodiments of the invention include an apparatus for tensioning an orthopedic surgical cable used in conjunction with an orthopedic implant device, a bone, and/or bone implant or structure. At least one device in accordance with various embodiments of the invention includes a handheld body capable of receiving a portion of the orthopedic surgical cable. The handheld body includes a clamping body adapted to restrain a first portion of the orthopedic surgical cable with an adjustable gripping force, wherein a tension is placed on the orthopedic surgical cable. The handheld body also includes an adjusting mechanism adapted to cooperate with the clamping body to change the gripping force on the orthopedic surgical cable. In addition, the handheld body includes a slide adapted to change the position of the clamping body relative to the handheld body. Furthermore, the handheld body includes a force application member operably connected to the slide, wherein the slide is adapted to be manipulated in order to change the position of the clamping body in a manner whereby the tension is subject to gradual control by manipulation of the slide and force application member, and whereby the handheld body and orthopedic surgical cable are adapted to allow the orthopedic surgical cable to be tensioned by the clamping body at a first tension, and further adapted to allow the orthopedic surgical cable to be subsequently tensioned by the slide and force application member at a second tension without loss of tension.

According to yet another aspect of the invention, systems, methods, and apparatuses according to various embodiments of the invention can include a method for using a surgical cable tensioning device with an orthopedic surgical cable for installation of the cable with respect to a patient's body. The method includes providing an orthopedic surgical cable and a surgical cable tensioning device, the surgical cable tensioning device comprising a handheld body, a clamping body, an adjusting mechanism, a slide, and a force application member. The method also includes mounting the orthopedic surgical cable relative to a bone in a patient's body. The method also includes restraining a first portion of the orthopedic surgical cable relative to the clamping body, wherein the clamping body can apply an adjustable clamping force on a portion of the orthopedic surgical cable, wherein a tension is placed on the orthopedic surgical cable. In addition, the method includes manipulating the adjusting mechanism to increase the clamping force on the portion of the orthopedic surgical cable. Furthermore, the method includes advancing the force application member with respect to the slide to change the position of the clamping body in a manner whereby the tension is subject to gradual control by manipulation of the force application member.

According to yet another aspect of the invention, systems, methods, and apparatuses according to various embodiments of the invention can include a surgical method for using a tensioning device with an orthopedic surgical cable for installation with respect to a patient's body. The method includes providing an orthopedic surgical cable and a tensioning device, the surgical cable clamp comprising a clamping body, a clamping mechanism, and a force application member. The method also includes mounting the orthopedic surgical cable to a bone in a patient's body. In addition, the method includes connecting a first portion of the orthopedic surgical cable to the clamping body. Furthermore, the method includes gripping the first portion of the orthopedic surgical cable within a portion of the clamping body by manipulating the adjusting mechanism in a first direction so that the consequent gripping is subject to gradual control by the adjustment mechanism, thus placing a first tension in the orthopedic surgical cable. The method also includes manipulating the force application member to change the position of the slide and clamping body, wherein the tension can be gradually increased. The method includes releasing the tension in the orthopedic surgical cable by manipulating the adjustment mechanism in a second direction so that the orthopedic surgical cable can be repositioned between the clamping mechanism and the clamping body. The method also includes gripping another portion of the orthopedic surgical cable within the portion of the clamping body by manipulating the adjusting mechanism in the first direction so that the consequent gripping is subject to gradual control by the adjustment mechanism, thus placing a second tension in the orthopedic surgical cable.

Objects, features and advantages of various systems, methods, and apparatuses according to various embodiments of the invention include:

(1) providing the ability to tension an orthopedic surgical cable without damaging the cable and creating the need to replace the cable; and (2) providing the ability to tension and retension an orthopedic surgical cable during the same surgical procedure.

Other aspects, features and advantages of various aspects and embodiments of systems, methods, and apparatuses according to the invention are apparent from the other parts of this document.

BRIEF DESCRIPTION OF THE DRAWINGS

FIG. 2 is an overhead view of a surgical cable tensioning device in accordance with an embodiment of the invention.

FIG. 3 is an end view of the surgical cable tensioning device shown in FIG. 2.

DETAILED DESCRIPTION OF SPECIFIC EMBODIMENTS

Systems, methods, and apparatuses according to various embodiments of the invention address some or all of the above issues and combinations thereof. They do so by providing a surgical cable tensioning device for tensioning and retensioning an orthopedic surgical cable used in conjunction with an orthopedic implant device, a bone, and/or bone implant or structure. The surgical cable tensioning device does not damage the orthopedic surgical cable when then the surgical cable tensioning device is operated or the surgical cable is tensioned or retensioned. While the surgical cable tensioning device is operated or in use, a tension can be placed and maintained on the orthopedic surgical cable without loss of tension. Furthermore, the surgical cable tensioning device can be reused along with the same surgical cable when the surgical cable tensioning device is unclamped and reclamped with respect to the surgical cable, while retensioning the surgical cable with respect to an orthopedic implant device, a bone, and/or bone implant or structure. Such systems, methods, and apparatuses are particularly useful for surgeons installing an orthopedic surgical cable within a patient's body, and attempting to tension and retension the orthopedic cable with respect to the installation of an orthopedic implant device, a bone, and/or bone implant or structure in the patient's body.

Figure 1:
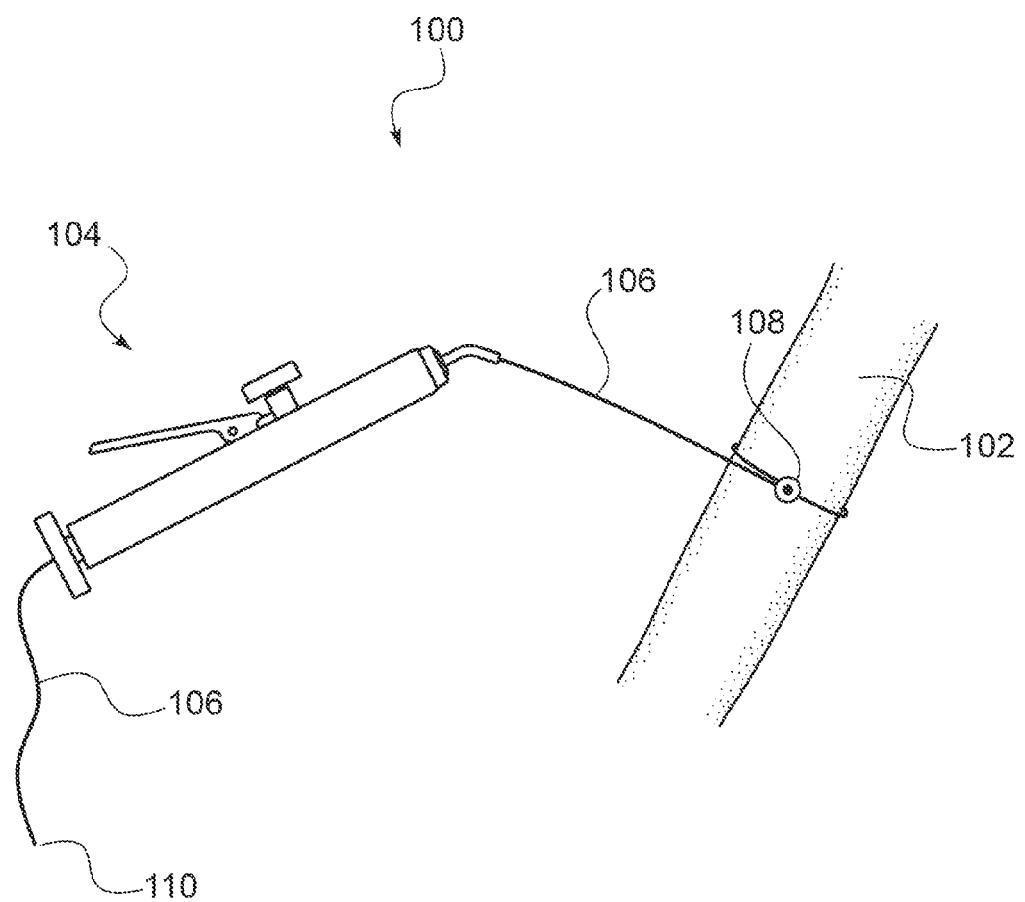
FIG. 1 is an exemplary environment for an embodiment of a surgical cable tensioning device in accordance with an embodiment of the invention.

FIG. 1 is an overhead view of a preferred environment for a surgical cable tensioning device in accordance with various embodiments of the invention. A preferred environment 100 shown in FIG. 1 is a portion of a human bone 102 in a surgical procedure. In the embodiment shown, a surgical cable tensioning device is a handheld surgical cable tensioning device 104 for tensioning an orthopedic surgical cable 106 relative to a portion of the patient's bone 102.

Typically, an orthopedic surgical cable 106 can be positioned with respect to a portion of a patient's bone 102 during a surgical procedure. One or more orthopedic surgical cables 106 can be utilized to secure any number of orthopedic devices, such as a bone plate, into a position relative to the patient's bone 102. Associated orthopedic devices, such as a cable clamp 108 can be used to secure a portion of the surgical cable with respect to the patient's bone. One end 110 of the orthopedic surgical cable 106 can be positioned through the cable tensioning device 104. When a force is applied to a cable tensioning device 104, the cable tensioning device 104 can grip a portion of the orthopedic surgical cable 108, thus restraining the orthopedic surgical cable 108 into a position relative to the patient's bone 102 and placing a tension in the cable tensioning device 104. When another force is applied to the cable tensioning device 104, the cable tensioning device 104 can gradually increase the tension in the orthopedic surgical cable 108 without loss of previously applied tension.

If necessary, the orthopedic surgical cable 108 can be loosened or otherwise retensioned by applying another force to the cable tensioning device 104 to relieve the gripping force on the orthopedic surgical cable 108 applied by the cable tensioning device 104. The orthopedic surgical cable 108 can then be retensioned by way of a cable tensioning device 104 so that the orthopedic surgical cable 108 is at a desired tension or position.

A surgical cable tensioning device in accordance with embodiments of the invention can be fashioned as a single or multiple component-type clamp. In any configuration, a surgical cable tensioning device is used to place and maintain a tension and, if necessary, change and increase the tension in an orthopedic surgical cable without loss of tension in the surgical cable. A surgical cable tensioning device in accordance with the invention can be used with other prefabricated orthopedic devices, such as a bone plate, that utilize orthopedic surgical cables for securing the device to a bone or another part of a patient's body. Finally, even though a surgical cable tensioning device in accordance with the invention is shown in FIG. 1 used in conjunction with an orthopedic surgical cable, a surgical cable tensioning device can be utilized with one or more surgical cables, or incorporated into another type of orthopedic device to be secured to an orthopedic surgical cable portion of a patient's body such as a bone or another body structure.

Figure 4:
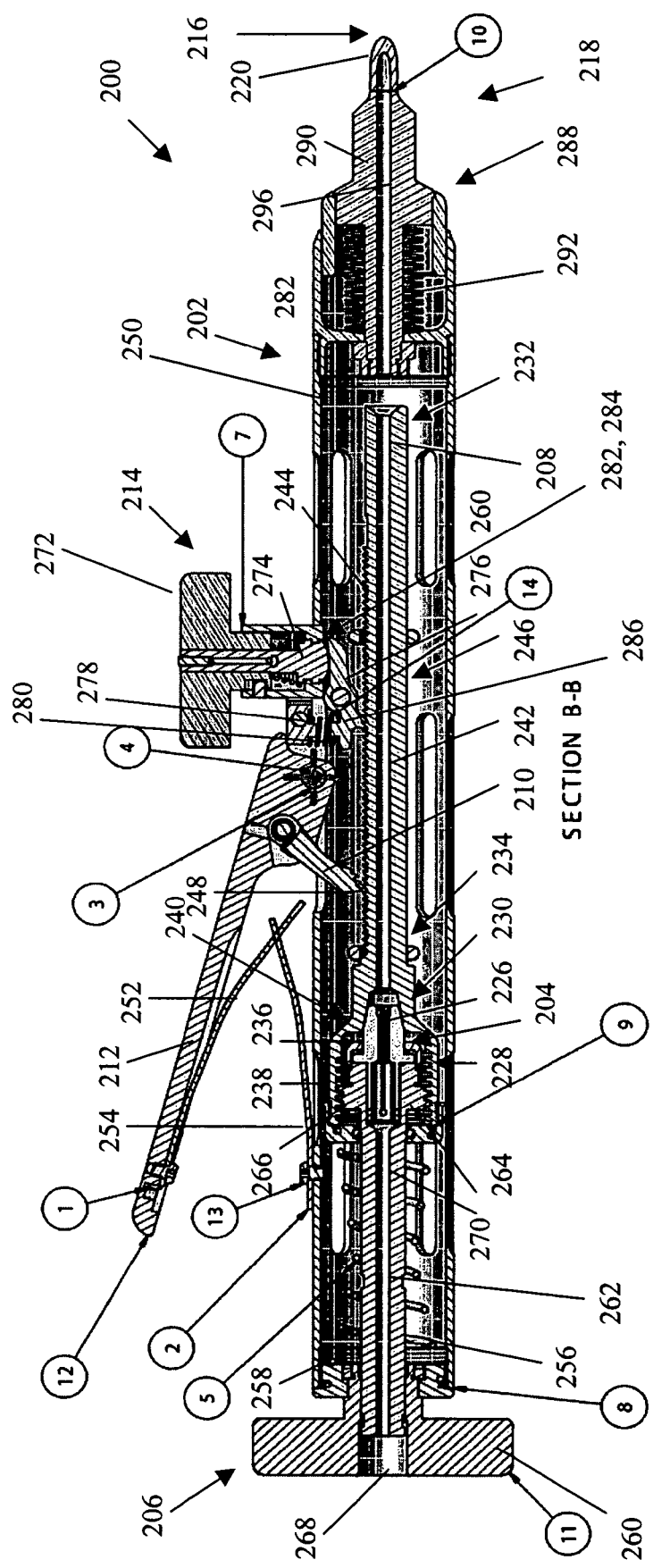
FIG. 4 is a side sectional view of the surgical cable tensioning device shown in FIG. 2.

FIG. 2 is an overhead view of an embodiment of a surgical cable tensioning device 200 similar to that shown as 104 in FIG. 1. FIG. 3 is an end view of the tensioning device 200 in FIG. 2, and FIG. 4 is a side-sectional view of the tensioning device 200 in FIG. 2 along line B-B. With reference to FIG. 4, the embodiment of a surgical cable tensioning device shown includes a handheld body 202, a clamping body 204, an adjusting mechanism 206, a slide 208, a force application member 210, a handle 212, and a release mechanism 214.

The handheld body 202 in this embodiment is a cylindrically-shaped hollow body capable of being held in a hand of a user, such as a surgeon. A cable input opening 216 adjacent to a cable input end 218 of the handheld body 202 is adapted to receive an end of an orthopedic surgical cable, such as 106 in FIG. 1. In the embodiment shown, the cable input opening 216 can be oriented adjacent to a relatively narrow, extended tubular-shaped portion or tip 220 of the handheld body 202.

The tip 220 shown in FIG. 2 has a slight curve such that the cable input opening 216 is offset from the central elongate axis 222 of the handheld body 202. One end of an orthopedic surgical cable 106 can be inserted into the cable input opening 216 and can extend through a portion of the tip 220 and handheld body 202 towards an opposing cable outlet end 224. A portion of the orthopedic surgical cable 106 can protrude from the cable output end 224. In one embodiment, a handheld body 202 can be pen-shaped and can be held by a user similar to a pen. In another embodiment, a handheld body 202 can have a pistol-type grip and can be held by a user similar to a pistol or handheld firearm. Other embodiments of a handheld body for an orthopedic surgical cable tensioning device in accordance with the invention can have alternative shapes and configurations, and may have fewer or greater numbers of components described herein.

The clamping body 204 and slide 208 shown in FIG. 4 can be oriented within the handheld body 202. In this embodiment, the clamping body 204 can be a collet-shaped device with a cable channel 226 between a relatively wide end 228 and a tapered end 230 that cooperates with corresponding-shaped portion of the slide 208. A portion of an orthopedic surgical cable, such as 106, can be positioned within a portion, or channel, of the clamping body. When a force is applied to the clamping body 204, such as a lateral force from the adjusting mechanism 206, a portion of the cable channel 226 can apply a gripping force to the orthopedic surgical cable 106 and restrain the position of the surgical cable 106 with respect to the clamping body 204. In other embodiments, a clamping body for an orthopedic surgical cable tensioning device can have other shapes or configurations in accordance with the invention.

The slide 208 shown in FIG. 4 can be an elongated cylindrically-shaped hollow body relatively smaller and shorter than the handheld body 202, and capable of fitting concentrically within the handheld body 202. An input end 232 of the slide 208 is adapted to receive a portion of an orthopedic surgical cable, such as 106, from the cable input end 232 of the handheld body 202. The opposing end 234 of the slide 208 is adapted to receive the clamping body 204 and a corresponding portion of the adjusting mechanism 206. In the embodiment shown, the cable input end 232 can include a relatively wide cavity 236 adapted to receive a portion of the clamping body 204. The cavity 236 can include a series of threads 238 which correspond to threads of the adjusting mechanism 206, and a tapered portion 240 to receive a corresponding portion of the clamping body 204, such as a tapered end of a collet-shaped device. A slide channel 242 can be sized to permit an orthopedic surgical cable, such as 106, to extend and protrude through a portion of the slide 208. The slide channel 242 can be aligned with the tapered portion 240 of the cavity 236, and the cable channel 226 of the clamping body 204 to permit an orthopedic surgical cable 106 to extend and protrude through the input end 232 of the slide 208, the cable channel 226 of the clamping body 204, and into the cavity 236. In other embodiments, a slide for an orthopedic surgical cable tensioning device can have other shapes or configurations in accordance with the invention.

In the example shown in FIG. 4, when a lateral force from the adjusting mechanism 206 is applied to the relatively wide end 228 of the clamping body 204, the tapered end 230 is forced or otherwise compressed against the corresponding-shaped portion of the slide 208 causing a portion of the cable channel 226 to become narrower. The narrowing of the cable channel 226 creates a gripping, clamping, or compression force on the surgical cable 106 as a portion of the cable channel 226 makes substantial contact with the portion of the surgical cable 106. As the lateral force on the clamping body 204 is increased, the cable channel 226 gradually and further narrows thereby increasing the gripping, clamping, or compression force on the surgical cable 106. Likewise, when the lateral force on the clamping body 204 is decreased, the cable channel 226 becomes wider, and the gripping, clamping, or compression force on the surgical cable 106 is correspondingly decreased.

The slide 208 shown in FIG. 4 is also adapted to travel with respect to the handheld body 202. A series of alternating notches and teeth 244, oriented along an external, intermediate portion 246 of the slide 208 can cooperate with the force application member 210. In one embodiment, cooperation between a slide and a force application member can be akin to a combination ratchet and pawl. The force application member 210 can include at least one protrusion 248 that can engage a corresponding notch between at least two teeth 244 along the slide 208. The force application member 210 shown in FIG. 4 can extend through a lateral side 250 of the handheld body 202, and can pivotably connect with a handle 212. In the example shown, the handle 212 can be lever shaped, and can separately mount adjacent to the lateral side 250 of the handheld body 202. In this manner, a user such as a surgeon can hold the handheld body 202 in his or her hand, and apply a manual force via the force application member 210 by gripping the handle 212 with the same hand and pumping the handle 212 towards the lateral side 250 of the handheld body 202.

Each time the handle 212 is pumped, the force application member 210 can be advanced with respect to the slide 208, and the slide 208 can be advanced towards cable output end 224 of the handheld body 202. For example, in the embodiment shown in FIG. 4, the protrusion 248 of the force application member 210 can advance one notch at a time along the series of teeth 244 of the slide 208 such that the slide 208 incrementally and gradually moves towards the cable output end 224 of the handheld body 202. In other embodiments, a force application member and handle for an orthopedic surgical cable tensioning device can have other shapes or configurations in accordance with the invention.

In the embodiment shown, a lever spring 252, such as a leaf spring, can mount to the handle 212, wherein the lever spring 252 is positioned between the handle 212 and the lateral side 250 of the handheld body 202. In addition, a body spring 254, such as a leaf spring, can mount to the lateral side 250 of the handheld body 202, wherein the body spring 254 is positioned between the handle 212 and the lateral side 250 of the handheld body 202. Either or both springs 252, 254 can provide a return force on the handle 212 when the user applies a manual force to the handle 212.

Furthermore, a slide return spring 256, such as a coil spring, can mount between the slide 208 and the cable output end 224 of the handheld body 202. For example, in the embodiment shown in FIG. 4, the slide return spring 256 is positioned within the handheld body 202 and between the cavity 236 and an internal end wall 258 of the handheld body 202 adjacent to the cable output end 224. In this manner, the position of the slide 208 can be returned to an initial position when the force application member 210 is no longer in contact with the slide 208. In the embodiment shown in FIG. 4, the release mechanism 214 described below can also cooperate with the slide 208 to resist the force of the slide return spring 256, and to control and maintain the position of the slide 208 as the force application member advances along the series of teeth 244 of the slide 208.

The adjusting mechanism 206 shown in FIG. 4 can include manually operated components for a user, such as a surgeon, to control and maintain the position of the slide 208 with respect to the handheld body 202. In addition, the adjusting mechanism 206 can permit a user to control and maintain the tension in an orthopedic surgical cable 106 facilitated by the cable tensioning device 200. The adjusting mechanism 206 shown in FIG. 2 can include a rotatable member such as a turning knob 260, a cylindrically-shaped hollow body 262, and a threaded head 264. A portion of the adjusting mechanism 206 can be oriented within the handheld body 202. As shown, the threaded head 264 can include a series of threads 266 which correspond to the threads 238 of the cavity 236 described above. The body 262 of the adjusting mechanism 206 can extend from the threaded head 264, through a portion of the handheld body 202, and towards the cable output end 224 of the handheld body 202. The turning knob 260 can mount to the extended body 262 of the adjusting mechanism 206, adjacent to the cable output end 224 of the handheld body 202. In this manner, a user such as a surgeon can apply a rotational force to the turning knob 260, and the extended body 262 can translate some or all of the rotational force to the threaded head 264. A cable output hole 268 within the turning knob 260 can be aligned with a channel 270 machined through the threaded head 264 and the extended body 262. The channel 270 can be sized to receive an orthopedic surgical cable, such as 106. When the threaded head 264, extended body 262, and cable output hole 268 are aligned, an orthopedic surgical cable 106 can be extended from the slide 208, and clamping body 204, through the channel 270, and through the cable output hole 268. In other embodiments, an adjusting mechanism for an orthopedic surgical cable tensioning device can have other shapes or configurations in accordance with the invention.

In this manner, an orthopedic surgical cable, such as 106, can initially be inserted through the handheld body 202. A leading portion of the surgical cable 106 can be inserted into the cable input opening 216 and through the corresponding channels of the slide 208, the clamping body 204, and the adjusting mechanism 206 until the leading portion of the surgical cable 106 protrudes through the cable output hole 268. When the desired position of the surgical cable 106 is attained, a user can manipulate the adjusting mechanism 206 by rotating the turning knob 260 in a first direction to apply a gradual gripping force to the portion of surgical cable 106 via the movement of the force application member 210 against the clamping body 204. As described above, the rotation of the turning knob 236 can be translated by the adjusting mechanism 206 to a lateral force upon the clamping body 204. As the lateral force increases, the gripping force of the clamping body 204 on the portion of surgical cable 106 increases. Likewise, when the turning knob 260 is rotated in an opposing, second direction the gripping force on the portion of surgical cable 106 adjacent to the clamping body 204 can be decreased. In the manner described above, the clamping body 204 can restrain the position of the orthopedic surgical cable 106 with respect to the handheld body 202, and a first tension can generated in the surgical cable 106.

When the user has sufficiently retained the position of the surgical cable 106 with respect to the handheld body 202, the user can manipulate the handle 212. Each time the handle 212 is pumped, the force application member 210 can be advanced with respect to the slide 208, and the slide 208 can be advanced towards cable output end 224 of the handheld body 202. For example, in the embodiment shown in FIG. 4, the protrusion 248 of the force application member 210 can advance one notch at a time along the series of teeth 244 of the slide 208 such that the slide 208 incrementally and gradually moves towards the cable output end 224 of the handheld body 202. In this example, the clamping body 204 retains the portion of the orthopedic surgical cable 106 while the position of the clamping body 204 moves in conjunction with the movement of the slide 208. In this manner, the tension in the orthopedic surgical cable 106 can be increased as the slide 208 and the clamping body 204 incrementally and gradually move towards the cable output end 224 of the handheld body 202 without a loss of tension in the orthopedic surgical cable 106. Alternatively, described in greater detail below, the tension in the orthopedic surgical cable 106 can be decreased when the slide 208 and the clamping body 204 incrementally and gradually move towards the cable input end 218 of the handheld body 202.

The release mechanism 214 shown in FIG. 4 can also include manually operated components for a user, such as a surgeon, to control and maintain the position of the slide 208 with respect to the handheld body 202. In addition, the release mechanism 214 can permit a user to control and maintain the tension facilitated by the cable tensioning device 200 on an orthopedic surgical cable 106. The release mechanism 214 shown in FIG. 4 can include a rotatable member such as a release knob 272, a threaded body 274, a pivotable release member 276, a return member 278, and spring 280. A portion of the release mechanism 214 can be oriented within the handheld body 202. As shown, the threaded body 274 can include a series of threads 282 which correspond to threads 284 adjacent to the lateral side 250 of the handheld body 202. The threaded body 274 can extend from the release knob 272, through a portion of the handheld body 202, and towards the slide 208 positioned within the handheld body 202. The release knob 272 can mount to an external end of the threaded body 274 of the release mechanism 214, while a portion of the threaded body 274 can contact or otherwise mount to the pivotable release member 276. The pivotable release member 276 can be lever-shaped and can mount to the lateral side 250 of the handheld body 202. One portion of the pivotable release member 276 can contact or otherwise mount to a portion of the threaded body 274, and another portion of the pivotable release member 276 can contact a portion of the slide 208. In this manner, a user such as a surgeon can apply a rotational force to the release knob 272, and the threaded body 274 can translate some or all of the rotational force to the pivotable release member 276.

The series of alternating notches and teeth 244 along the external, intermediate portion of the slide 208 can also cooperate with the pivotable release member 276 or another portion of the release mechanism 214. In one embodiment, cooperation between a slide and pivotable release member 276 or another portion of the release mechanism 214 can be akin to a combination ratchet and pawl. The pivotable release member 276 or another portion of the release mechanism 214 can include at least one protrusion 286 that can engage a corresponding notch between at least two teeth 244 along the slide 208. The pivotable release member 276 shown in FIG. 4 can connect with and pivot with respect to the lateral side 250 of the handheld body 202.

The return member 278 and spring 280 can generate a return force on the pivotable release member 276 to counter some or all of the force applied to the release knob 272. The return member 278 can mount to the lateral side 250 of the handheld body 202, and can further mount to or otherwise connect with a portion of the pivotable release member 276. In the embodiment shown in FIG. 4, the protrusion 286 of the pivotable release member 276 is positioned on a lower portion of the pivotable release member 276, and contact or connection with the return member 278 is with an upper portion of the pivotable release member 276. The spring 280 can be positioned between pivotable release member 276 and a surface of the return member 278 or an internal surface of the handheld body 202. In other embodiments, a release mechanism for an orthopedic surgical cable tensioning device can have other shapes or configurations in accordance with the invention.

To release a previously generated tension on a surgical cable using a cable tensioning device 200, a user such as a surgeon can hold the handheld body 202 in his or her hand, and apply a manual force via the release mechanism 214 by gripping the release knob 272 with the other hand and rotating the release knob 272 in one direction. If a user desires to maintain tension in an orthopedic surgical cable 106, the user can rotate the release knob 272 in one opposing direction to move the pivotable release member 276 towards and into contact with the slide 208. In each instance, the rotation can manipulate the position of the pivotable release member 276 towards the slide 208 or away from the slide 208. In some instances, if a user desires to release a tension in an orthopedic surgical cable, such as 106, the user can rotate the release knob 272 to move the pivotable release member 276 away from and out of contact with the slide 208.

In the embodiment shown, the functionality of the release mechanism 214 can cooperate with the functionality of the force application member 210, such that when both the force application member 210 and the release mechanism are simultaneously manipulated, the slide 208 can change position or return to an initial position and release a previously generated tension in the orthopedic surgical cable 106. In other embodiments, the functionality of a release mechanism can operate independently from the functionality of a force application member to permit the slide to change position to release a tension in the orthopedic surgical cable 106. In another embodiment, a force application member and release mechanism can cooperate to permit gradual and incremental decreases in a previously generated tension in an orthopedic surgical cable 106.

The surgical cable tensioning device 200 in FIG. 4 can also include a tension load assembly 288. The tension load assembly 288 shown can be adapted to measure a force being applied by the surgical cable tensioning device 200. In this example, the tension load assembly 288 can include a head element 290, a spring 292, and an output display 294 (shown in FIG. 2). The head element 290 can be a tapered and positioned between the slide 208 and the tip 220 of the surgical cable tensioning device 200. A head channel 296 machined through a portion of the head element 290 is adapted to receive a portion of an orthopedic surgical cable, such as 106, and can be aligned with the tip 220 and the slide 208. The spring 292, such as a coil spring, can be positioned adjacent to a portion of the head element 290, and further positioned between the head element 290 and an internal surface of the surgical cable tensioning device 200. The spring 292 is adapted to provide a return force on a portion of the head element 290 when a force is applied to either or both the tip 220 and head element 290.

When the head channel 296 is aligned with the tip 220 and the slide 208, an orthopedic surgical cable, such as 106, can be inserted within the cable input opening 216, and pushed through the tip 220 and into the slide channel 242. In this manner, when a force is applied to the orthopedic surgical cable 106 adjacent to the cable input opening 216, the force may cause the tip 220 and head element 290 to change position relative to the handheld body 202, and move towards the cable output end 224 of the handheld body 202. This type of movement will cause the spring 292 to compress, and a return force in the spring 292 will be generated. Shown in FIG. 2, the output display 294, such as a cutout in the lateral side 250 of the handheld body 202, can be viewed by a user, such as a surgeon. Predefined measurements of force can be designated on the handheld body 202 adjacent to the output display 294. In this manner, a user can determine the amount of force or tension that the surgical cable tensioning device 200 may be applying to the orthopedic surgical cable 106. In some embodiments, an output display can be an electronic device adapted to measure or display an output measurement of a force on the spring 292, tension on a surgical cable, or force on another component of the surgical cable tensioning device 200. In other embodiments, a tension load assembly for an orthopedic surgical cable tensioning device can have other shapes or configurations in accordance with the invention. In some embodiments, a tension load assembly and associated functionality may be omitted from an orthopedic surgical cable tensioning device.

Various components of a surgical cable tensioning device such as 200 can be manufactured from titanium, stainless steel, cobalt chromium alloy, or another similar type of material. An example of a surgical cable tensioning device 200 measures approximately 12 inches (30.4 cm) in length parallel with the central axis of the device, approximately 1 inch (2.5 cm) in width, and approximately 2.5 inches (6.3 cm) in height from the extended tip of the handle to a lower portion of the handheld body. Furthermore, an example of a surgical cable that can be used with the surgical cable tensioning device 200 is typically a cobalt chromium or stainless steel cable measuring approximately 0.04 to 0.08 inches (1.0 to 2.0 mm) in diameter.

The surgical cable tensioning device 200 is a preferred embodiment of a surgical cable tensioning device in accordance with the invention. Other embodiments of surgical cable tensioning device can be used in the preferred environment and other similar type environments to accomplish similar functions in accordance with the invention.

Figure 5A:
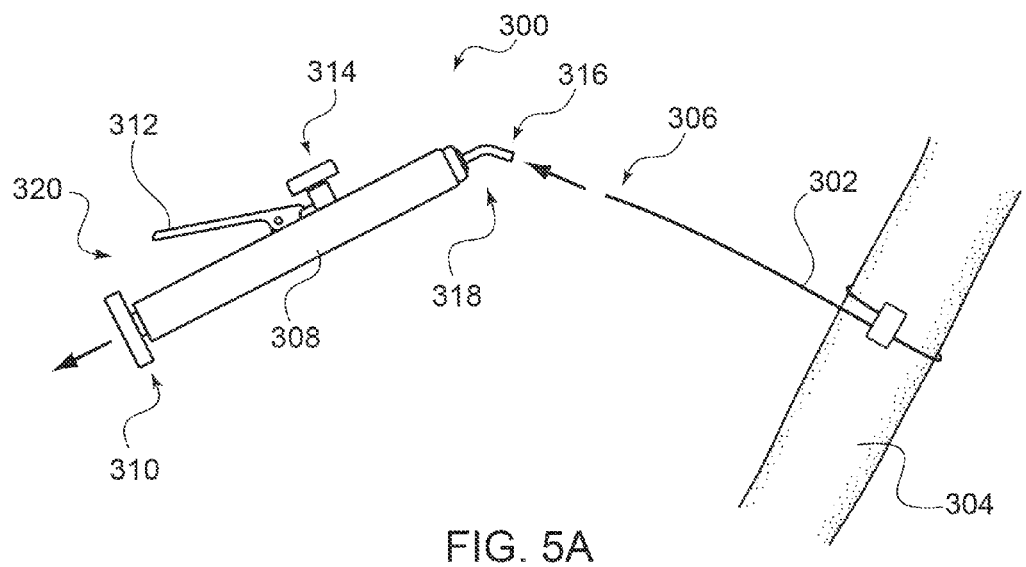
FIGS. 5A-5C illustrate a sequence for a method for using the surgical cable tensioning device shown in FIGS. 2-4.
Figure 5B:
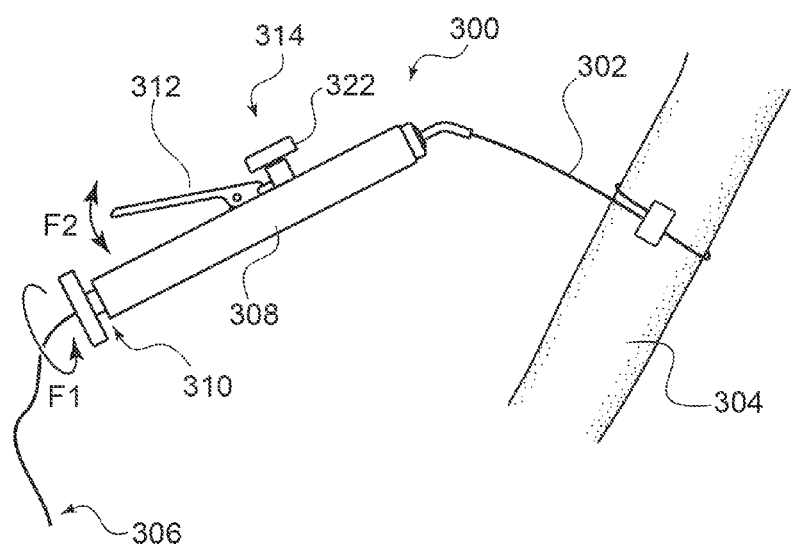
Figure 5C:
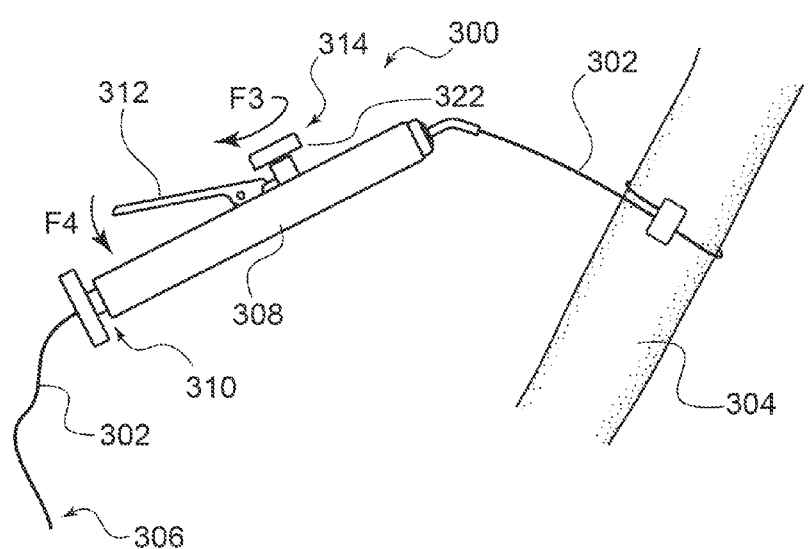

FIGS. 5A-5C illustrate a sequence for a method for using the surgical cable tensioning device shown in FIGS. 2, 3, and 4. The particular embodiment shown in this sequence utilizes a surgical cable tensioning device, shown in FIGS. 2, 3, and 4 as 200. Other embodiments of a surgical cable tensioning device can be utilized with the method illustrated in FIGS. 5A-5C.

In FIG. 5A, a surgical cable tensioning device 300 in accordance with the invention is shown adjacent to an orthopedic surgical cable 302. As shown, a user such as a surgeon can hold the surgical cable tensioning device 300 in his or her hand. The user can align the surgical cable 302 with a proximal end of a patient's bone 304 in accordance with a surgical procedure. When the surgical cable 302 is to be secured to the patient's bone 304, the surgical cable tensioning device 300 is positioned in a desired position adjacent to a portion of the surgical cable 302, such as a leading end 306, to receive the leading end 306 of the surgical cable 302. Typically, an opposing end of the surgical cable is connected to, secured to, or otherwise mounted to the bone 304 via a cable clamp, orthopedic device, or other surgical device. Similar to the surgical cable tensioning device 300 in FIGS. 2-4, the surgical cable tensioning device 300 shown includes a handheld body 308, a slide (not shown), a force application member (not shown), an adjusting mechanism 310, a handle 312, and a release mechanism 314, and can be assembled and operated as described in FIG. 2. The leading end 306 of a predetermined length of surgical cable 302 is inserted into and pushed through a cable inlet hole 316 adjacent to a cable input end 318 of the surgical cable tensioning device 300. The surgical cable 302 is pushed through the handheld body 308, and into a position adjacent to at least the clamping body inside the handheld body 308 until the leading end 306 protrudes through a cable outlet hole adjacent to a cable outlet end of the surgical cable tensioning device 300. When the surgical cable tensioning device 300 is positioned with respect to the surgical cable 302, a user such as a surgeon can manipulate the adjusting mechanism 310 in a first direction to apply a gradual gripping force to the portion of surgical cable 302 via the movement of the adjusting mechanism 310 against the clamping body. As needed, the adjusting mechanism 310 can be rotated to gradually increase the gripping force of the clamping body on the portion of surgical cable 302. Likewise, as needed, the adjusting mechanism 310 can rotated in an opposing, second direction to decrease the gripping force on the portion of surgical cable 302 adjacent to the clamping body. In this manner, the clamping body can restrain the position of the orthopedic surgical cable 302 with respect to the clamping body and the handheld body 308, and a first tension can generated in the surgical cable 302.

As shown in FIG. 5B, the user can apply a manual force via the force application member by gripping the handle 312, with the same hand holding the handheld body 308, and pumping the handle 312 towards the lateral side 318 of the handheld body 308. Each time the handle 312 is pumped, the force application member can be advanced with respect to the slide, and the slide and clamping body can be advanced towards the cable output end 320 of the handheld body 308. For example, the surgical cable tensioning device 300 can include a force application member, clamping body, and slide similar to the force application member 210, clamping body 204, and slide 208 described and shown in FIGS. 2-4. In this manner, the tension in the surgical cable 302 can be gradually increased without loss of tension. When a desired second tension in the surgical cable 302 is attained, the user can cease pumping the handle 312. Any excess length of surgical cable 302 can be trimmed with a cutting instrument (not shown).

If, for any reason, the tension is not sufficient or desired, the user may release the tension in the cable. As shown in FIG. 5C, the user can hold the handheld body 308 in his or her hand, and apply a manual force via the release mechanism 314 by gripping a release knob 322 with the other hand and rotating the release knob 322 in one direction. Rotation of the release knob 322 manipulates the position of the pivotable release member (not shown) towards the slide or away from the slide. For example, the surgical cable tensioning device 300 can include a slide, release mechanism, rotating knob, and pivotable release member similar to the slide 208, release mechanism 214, turning knob 260, and pivotable release member 276 described and shown in FIGS. 2-4. In some instances, if a user desires to release tension in an orthopedic surgical cable, such as 106, the user can rotate the release knob 322 in one direction to move the pivotable release member away from and out of contact with the slide. In other instances, if a user desires to maintain tension in an orthopedic surgical cable 302, the user can rotate the release knob 322 in an opposing direction to move the pivotable release member towards and into contact with the slide.

More than one surgical cable may be needed to secure an orthopedic device such as a cable clamp or bone plate to a patient's bone 304. The above sequence can be repeated as needed until cable clamp, bone plate, or other orthopedic device is secured to the patient's bone. After tensioning one or more surgical cables 302 to the patient's bone with surgical cable tensioning device 300, previously tensioned surgical cables may tend to loosen or otherwise require additional tension to sufficiently secure the cable clamp, bone plate, or other orthopedic device to the patient's bone 304. If necessary, the tension on a previously tensioned surgical cable can be released by applying an untightening force to the cable clamp, bone plate, or other orthopedic device with an untightening instrument, thus releasing the compression and tension on the surgical cable 302. The surgical cable 302 can then be retensioned manually or by use of the surgical cable tensioning device 300. When the desired tension is reached using the surgical cable tensioning device 300, the position of the surgical cable 302 should be relatively stable relative to the patient's bone 304 and cable clamp, bone plate, or other orthopedic device.

Tensioning and retensioning of one or more surgical cables 302 may occur more than once during a surgical procedure until all of the surgical cables 302 are sufficiently tensioned to maintain the position of the surgical cables 302, and cable clamp, bone plate, or other orthopedic device relative to the patient's bone 304. The sequence described above with respect to FIGS. 5A-5C can be repeated as necessary to accomplish this.

While the above description contains many specifics, these specifics should not be construed as limitations on the scope of the invention, but merely as exemplifications of the disclosed embodiments. Those skilled in the art will envision many other possible variations that within the scope of the invention as defined by the claims appended hereto.

The invention claimed is:

1. A tensioning device for an orthopedic surgical cable, wherein the orthopedic surgical cable is adapted to be installed relative to a bone in a patient, comprising:
a handheld body capable of receiving a portion of the orthopedic surgical cable, having a cable input opening and a cable output end, the handheld body comprising
a clamping body adapted to restrain a first portion of the orthopedic surgical cable with an adjustable gripping force;
wherein the clamping body is a collet that defines an opening for receiving the orthopedic surgical cable such that the opening substantially surrounds the first portion of the orthopedic surgical cable;
wherein the opening in the clamping body is adjustable such that at least a portion of the opening can be narrowed to engage the clamping body around the first portion of the orthopedic surgical cable;
an adjusting mechanism adapted to at least narrow the opening in the clamping body to engage the clamping body around the first portion of the orthopedic surgical cable;
a slide adapted to change the position of the clamping body relative to the handheld body, wherein a working length of the slide fits within the handheld body, and wherein the slide has a series of alternating notches and teeth;
a force application member operably interfacing with the slide over said working length, wherein the force application member has a protrusion adapted to engage the notches between the teeth of the slide, wherein the slide is adapted to be manipulated in order to change the position of the clamping body in a manner whereby a tension force on the orthopedic surgical cable is subject to gradual control by manipulation of the slide and force application member;
a slide return spring;
a release mechanism adapted to cooperate with the slide and to resist the force of the slide return spring in order to control and maintain the position of the slide as the force application member advances along the slide, whereby the handheld body is adapted to allow the orthopedic surgical cable to be tensioned by the clamping body at a first tension, to be subsequently tensioned by the slide and force application member at a second tension without loss of tension while tensioning to the second tension.

2. The tensioning device of claim 1, further comprising:
a handle operably connected to the force application member, wherein the handle is adapted to be manipulated to actuate the force application member.

3. The tensioning device of claim 1, wherein:
the adjusting mechanism comprises a rotatable member.

4. The tensioning device of claim 1, wherein:
the force application member is adapted to advance the slide with respect to the handheld body.

5. The tensioning device of claim 1, wherein:
the slide is adapted to retain a portion of the clamping body, and the slide is further adapted to permit the force application member to advance along a portion of the slide.

6. The tensioning device of claim 1, wherein:
the slide comprises a ratchet, and
the force application member comprises a pawl.

7. The tensioning device of claim 1, wherein:
the adjusting mechanism has a threaded portion and the slide has a threaded portion, and wherein the threaded portion of the adjusting mechanism is adapted to engage the threaded portion of the slide.

8. The tensioning device of claim 1, wherein:
the release mechanism has a threaded portion and the handheld body has a threaded portion, and wherein the threaded portion of the release member is adapted to engage the threaded portion of the handheld body.

9. The tensioning device of claim 1, wherein at least a portion of the opening in the handheld body extends along a longitudinal axis.

10. The tensioning device of claim 9, wherein the clamping body is positioned inside of the handheld body.

11. The tensioning device of claim 10, wherein the opening in the clamping body is adjustable such that the portion of the opening in the clamping body can be narrowed to exert substantially equal clamping forces about a circumference of the first portion of the orthopaedic surgical cable.

12. The tensioning device of claim 11, wherein moving the clamping body in a first direction along the longitudinal axis imparts said tension to the orthopaedic surgical cable.

13. The tensioning device of claim 12, wherein moving the clamping body in a second direction along the longitudinal axis narrows the portion of the opening in the clamping body.

14. The tensioning device of claim 13, wherein the portion of the opening in the clamping body is a cylindrical opening.

15. The tensioning device of claim 14, wherein movement of the clamping body in the second direction moves portions of the clamping body into contact with or further contact with the slide to narrow the cylindrical opening.

16. The tensioning device of claim 15, wherein the clamping body includes a tapered surface for cooperation with a corresponding surface of the slide to facilitate narrowing the cylindrical opening.

17. The tensioning device of claim 16, wherein the release mechanism is biased against the slide to prevent the slide from moving in the second direction.

18. The tensioning device of claim 17, wherein the release mechanism is biased in engagement with the slide to prevent the slide from moving in the second direction.

19. The tensioning device of claim 18, further comprising an actuator for at least temporarily counteracting the bias of the release mechanism against the slide such that the release mechanism does not prevent the slide from moving in the second direction.

20. The tensioning device of claim 19, wherein actuating the actuator pivots an engagement portion of the release mechanism away from the slide such that the release mechanism does not prevent the slide from moving in the second direction.

21. The tensioning device of claim 1, wherein the opening in the handheld body is curved at a first end of the handheld body.

22. The tensioning device of claim 1, wherein the opening in the handheld body extends proximate a tension measurer.

23. The tensioning device of claim 22, wherein the opening in the handheld body extends through the tension measurer.

* * * * *